United States Patent [19]

Little et al.

[11] Patent Number: 4,628,939
[45] Date of Patent: Dec. 16, 1986

[54] METHOD AND IMPROVED APPARATUS FOR ANALYZING HEART ACTIVITY

[75] Inventors: Michael J. Little, Tarzana; Harry A. Dellamano, Thousand Oaks, both of Calif.

[73] Assignee: Hughes Aircraft Company, Los Angeles, Calif.

[21] Appl. No.: 550,350

[22] Filed: Nov. 10, 1983

Related U.S. Application Data

[62] Division of Ser. No. 186,041, Sep. 11, 1980, Pat. No. 4,428,380.

[51] Int. Cl.$^4$ .............................................. A61B 4/00
[52] U.S. Cl. .................................... 128/696; 128/715
[58] Field of Search ............... 128/696, 731, 708, 901, 128/902, 908

[56] References Cited

U.S. PATENT DOCUMENTS

| | | | |
|---|---|---|---|
| Re. 27,042 | 1/1971 | Jorgensen et al. | 128/2.05 |
| 2,073,457 | 3/1937 | Schwarzschild | 128/2.05 |
| 2,294,015 | 8/1942 | Salb et al. | 128/2.06 |
| 2,362,830 | 11/1944 | Kline | 179/171.5 |
| 2,457,744 | 12/1948 | Sturm | 128/2.06 |
| 2,634,611 | 4/1953 | Johnson | 73/410 |
| 2,635,183 | 4/1953 | Smith et al. | 250/17 |
| 2,689,161 | 9/1954 | Marchano et al. | 346/33 |
| 2,946,645 | 7/1960 | Schwarzer | 346/33 |
| 3,030,946 | 4/1962 | Richards | 128/2.06 |
| 3,048,166 | 8/1962 | Rodbard | 128/2.06 |
| 3,052,233 | 9/1962 | Veling | 128/2.1 |
| 3,052,756 | 9/1962 | Seven et al. | 179/1 |
| 3,058,458 | 10/1962 | Daneman | 128/2.06 |
| 3,132,208 | 5/1964 | Dymski et al. | 179/1 |
| 3,140,710 | 7/1964 | Glassner et al. | 128/2.05 |
| 3,171,406 | 3/1965 | Baum et al. | 128/2.05 |
| 3,188,645 | 6/1965 | Trumpy et al. | 346/33 |
| 3,215,136 | 11/1965 | Holter et al. | 128/2.06 |
| 3,229,687 | 1/1966 | Holter et al. | 128/2.06 |
| 3,236,239 | 2/1966 | Berkovits | 128/419 |
| 3,267,933 | 8/1966 | Mills et al. | 128/2.06 |

(List continued on next page.)

FOREIGN PATENT DOCUMENTS 1130906 2/1957 France.
787743 12/1957 United Kingdom.
209621 4/1968 U.S.S.R..
523690 10/1976 U.S.S.R..
674744 7/1979 U.S.S.R..

OTHER PUBLICATIONS

Andree, C. "An Impact Strain Gage" Instruments, May 1931, pp. 265–275.
Spurlock, J. et al, "Recording Infant Heart Rate Patterns in the Home" Jr. of Assc. for Adv. of Medical Insturmation, Sep.–Oct. 1971, pp. 290–296.
Rositano, S. et al, "Ultra Soft Dry Electrodes for Electrocardiography", Jr. of Assc. for Adv. of Med. Instr., Jan./Feb., 1973, p. 41.
Nilsson, K. et al, "A Combined Microphone for Simultaneous Recording of Pulse and Heart Sounds, Biomed. Eng., Oct. 1973, pp. 424–425.
Nilson, K. et al, "A Combined Microphone for Simultaneous Recording of Pulse, Phono and Reference ECG", Electro-Medica, Feb. 76, pp. 64–68.
Geddes, L. A. et al, "The Use of the Same Pair of Dry Electrodes to Record Skin Resistance and Beat-By—

List Continued on next page.

Primary Examiner—Kyle L. Howell
Assistant Examiner—Francis J. Jaworski
Attorney, Agent, or Firm—Victor G. Laslo; A. W. Karambelas

[57] ABSTRACT

A method and associated means for producing simultaneous electrical representations of the electrical and acoustical (heart sound) activity of the heart, in which a pickup device and associated circuits produce a full wave rectified symmetrical heart sound signal annotated by pulses developed from the QRS wave of the electrocardiogram signal.

The pickup device is designed to permit the direct (unbuffered) application of the pickup electrodes to the skin of the body and to provide a control of the associated circuits when not in contact with the body to shorten response times when the pickup device is placed in contact with the body.

4 Claims, 15 Drawing Figures

U.S. PATENT DOCUMENTS

| | | | |
|---|---|---|---|
| 3,318,303 | 5/1967 | Hammacher | 128/672 |
| 3,323,515 | 6/1967 | Foner et al. | 128/2.06 |
| 3,339,543 | 9/1967 | Richard | 128/2.06 |
| 3,342,176 | 9/1967 | Kaplan et al. | 128/2.06 |
| 3,348,535 | 10/1967 | Gregg | 128/2.05 |
| 3,380,445 | 4/1968 | Frasier | 128/2.06 |
| 3,388,377 | 6/1968 | Folsom et al. | 340/146.1 |
| 3,405,707 | 10/1968 | Edwards | 128/2.05 |
| 3,455,293 | 7/1969 | Bethune | 128/2.05 |
| 3,457,452 | 7/1969 | Saper | 315/19 |
| 3,495,584 | 2/1970 | Schwalm | 128/2.06 |
| 3,498,290 | 3/1970 | Shaw et al. | 128/2.05 |
| 3,542,013 | 11/1970 | Stephenson | 128/2.06 |
| 3,547,105 | 12/1970 | Paine et al. | 128/2.06 |
| 3,559,193 | 11/1971 | Savaglio et al. | 128/908 X |
| 3,565,060 | 2/1971 | Sipple | 128/2.06 |
| 3,569,852 | 3/1971 | Berkovits | 128/901 X |
| 3,580,241 | 5/1971 | Weinstein | 128/2.06 |
| 3,585,988 | 6/1971 | Creigh et al. | 128/2.06 |
| 3,601,120 | 8/1971 | Massie | 128/2.05 S |
| 3,602,215 | 8/1971 | Parnell | 128/2.06 B |
| 3,616,791 | 11/1971 | Harris | 128/2.06 A |
| 3,620,208 | 11/1971 | Higley et al. | 128/2.06 E |
| 3,621,844 | 11/1971 | Hayashi et al. | 128/2.05 R |
| 3,623,477 | 11/1971 | Trent | 128/2.1 B |
| 3,624,744 | 11/1971 | Munger | 128/2.05 R |
| 3,628,527 | 12/1971 | West | 128/2.06 B |
| 3,652,999 | 3/1972 | Hjort et al. | 340/172.5 |
| 3,699,948 | 10/1972 | Ota et al. | 128/2.06 G |
| 3,703,168 | 11/1972 | Frink | 128/2.06 R |
| 3,744,482 | 7/1973 | Kaufman et al. | 128/2.06 E |
| 3,745,407 | 7/1973 | Day | 315/30 |
| 3,762,397 | 10/1973 | Cage | 128/2.05 S |
| 3,769,964 | 11/1973 | Smith | 128/2.05 G |
| 3,773,033 | 11/1973 | Rodbard et al. | 128/2.06 R |
| 3,776,221 | 12/1973 | McIntyre | 128/2.05 R |
| 3,793,626 | 2/1974 | Zambuto | 340/172.5 |
| 3,799,147 | 3/1974 | Adolph et al. | 128/2.05 S |
| 3,799,148 | 3/1974 | Rowen | 128/2.06 A |
| 3,830,227 | 8/1974 | Green | 128/2.06 R |
| 3,835,455 | 9/1974 | Abbenante | 340/172.5 |
| 3,846,585 | 11/1974 | Slosberg et al. | 179/1 ST |
| 3,853,119 | 12/1974 | Peterson et al. | 128/2.06 R |
| 3,858,005 | 12/1974 | Marshall et al. | 179/1 ST |
| 3,858,576 | 1/1975 | Dehnert et al. | 128/2.06 R |
| 3,868,947 | 3/1975 | Holsinger | 128/2.06 E |
| 3,868,948 | 3/1975 | Graetz | 128/2.06 G |
| 3,874,370 | 4/1975 | Harris et al. | 128/2.06 A |
| 3,878,832 | 4/1975 | Tickner et al. | 128/2.05 S |
| 3,878,833 | 4/1975 | Arneson et al. | 128/2.05 A |
| 3,895,316 | 7/1975 | Fein | 332/17 |
| 3,909,792 | 9/1975 | Harris et al. | 340/172.5 |
| 3,911,903 | 10/1975 | Gee et al. | 128/2.05 Q |
| 3,921,623 | 11/1975 | Okada et al. | 128/2.05 P |
| 3,939,824 | 2/1976 | Arneson et al. | 128/2.05 A |
| 3,940,742 | 2/1976 | Hudspeth et al. | 340/172.5 |
| 3,954,100 | 5/1976 | Sem-Jacobsen | 128/2.06 E |
| 3,960,141 | 7/1976 | Bolduc | 128/2.06 E |
| 3,995,259 | 11/1976 | Harris et al. | 340/172.5 |
| 4,006,737 | 2/1977 | Cherry | 128/2.06 G |
| 4,016,871 | 4/1977 | Schiff | 128/2.06 R |
| 4,053,951 | 10/1977 | Hudspeth et al. | 364/415 |
| 4,071,694 | 1/1978 | Pfeiffer | 179/1 ST |
| 4,088,138 | 5/1978 | Diack et al. | 128/419 D |
| 4,094,308 | 6/1978 | Cormier | 128/2.05 R |
| 4,119,090 | 10/1978 | Dehnert | 128/2.06 G |
| 4,154,231 | 5/1979 | Russell | 128/663 |
| 4,182,315 | 1/1980 | Vas et al. | 128/687 |
| 4,187,858 | 2/1980 | Day et al. | 128/710 |
| 4,331,157 | 5/1982 | Keller, Jr. et al. | 128/696 |

OTHER PUBLICATIONS

Beat Heart Rate," Med. & Biol. Eng., Jan. 1975, pp. 89–96.

Karpman, L. et al, "Sound Envelope Averaging and the Differential Diagnosis of Systolic Murmurs", Amer. Heart Jr., Nov. 1975, pp. 600–606.

Betts, R. P. et al, "Method for Recording Electrocardiograms with Dry Electrodes Applied to Unprepared Skin", Med. & Biol. Engr., Jan. 1975, pp. 89–96.

Tiberghiem, J. et al, "An Active Probe for Electrocardiography", Oct. 21, 1980, pp. 249–250.

Webster, J. G., "Dry Electrodes", Medical Instrumentation, 1974, pp. 247–250.

Orias, O. et al, "The Heart Sounds in Normal and Pathological Conditions", Oxford Medical Publications 1939, pp. 18–40.

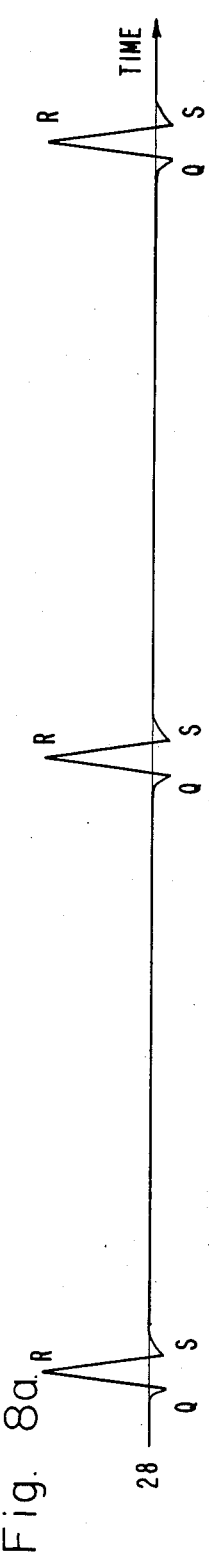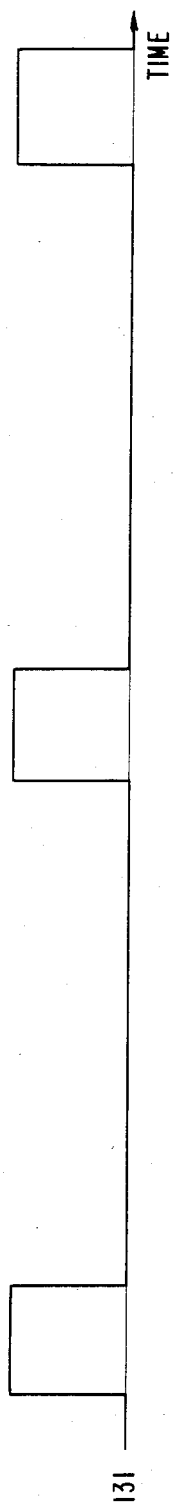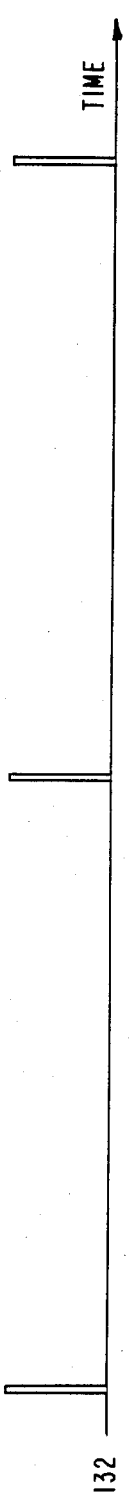

METHOD AND IMPROVED APPARATUS FOR ANALYZING HEART ACTIVITY

This is a division of application Ser. No. 186,041, filed Sept. 11, 1980, now U.S. Pat. No. 4,428,380.

TECHNICAL FIELD

This invention relates to an improved, reliable method for the analysis of heart activity and includes within its scope apparatus specially adapted for the practice of such method. more particularly, the method and the apparatus therefor relate to the practices of auscultation and phonocardiography and their use in the detection of heart activity and/or abnormalities.

BACKGROUND OF THE INVENTION

The heart cycle provides both electrical and audio (or phono) signals containing invaluable diagnostic information for the practicing physician. The electrical system of the heart includes a pacemaker or electrical generating source near the right atrium known as the sinoatrial (SA) node. When the SA node generates an electrical pulse, that pulse is transmitted to both atria causing them to contract to force blood through the atrio-ventricular valves and into the ventricles. The generated wave pulse then reaches a atrio-ventricular (A/V) node, which slows down the speed of the impulse to allow the blood to flow from the atria to the respective ventricles. After a time delay of about 100 milliseconds, this impulse is then transmitted to the ventricles through the Purkinge fibers, effecting contraction of the ventricles. Thereafter, the ventricles relax. The above named electrical sequence occurs for each beat of the normal heart.

The aforementioned transmitted pulse effects the electrical depolarization of the heart muscle fibers. Repolarization of the heart muscle occurs upon relaxation. Depolarization and repolarization are electrically measurable phenomena and form the basis for the well known electrocardiogram (ECG) measurement of heart activity. The ECG analog waveform associated with the described heart activity includes a number of medically significant segments. In the case of a normal "at rest" heartbeat, there first occurs a "P wave". This "P wave" comprises a small rise and drop in the analog signal amplitude. This wave is representative of the depolarization of the atria and is immediately followed by a generally short level signal portion which terminates in a drop in signal amplitude. This drop is referred to as the "Q wave". The portion of the ECG between the end of the "P wave" and the beginning of the "Q wave" is called "PQ interval" or "PQ segment". Physiologically, this interval represents a pause in the heart sequence and corresponds to the flow of blood from the atria into the ventricles.

Following the "Q wave" there is a rapid rise in the signal voltage to maximum amplitude known as the "R wave". A corresponding sharp drop in voltage amplitude to below the level of the "PQ interval" followed by a rise back to such level is characterized as the "S wave". The "S wave" is then followed first by a level segment which terminates in a further rise and fall in amplitude known as the "T wave". The point where the "S wave" terminates in the beginning of the level segment is known as the "J point", and the level segment between the end of the "S wave" and the start of the "T wave" is known as the "ST segment". The Q, R, and S waves are referred to as the "QRS complex" and represent ventricular contraction (depolarization). The "T wave" represents repolarization of the ventricles. After the "T wave" there is a brief, further level segment before the commencement of the "P wave" of the next heart beat. This latter segment is referred to as the "TP segment". Thus, the various heart activities are well defined in terms of the electrical impulses. The various ECG segments illustrated with respect to a normal "at rest" heart are shown in the electrocardiogram of FIG. 1.

Just as the heart cycle is characterized by the above-referenced sequence of electrical events, it is similarly characterized by a sequence of acoustical events. Normally, the most significant of these events are denominated "Heart Sound I" (HS I) and "Heart Sound II" (HS II) although additional heart sounds of significance may be identified. The identification of information as a particular heart sound is critical for diagnostic purposes. Although the sounds are defined by different frequency bands (HS I, for instance, is in the medium high and high frequency audio range of 100 to 1000 cycles per second while HS II is in the medium low frequency range of 50 to 100 cycles per second), the physician, especially one having a hearing impediment, is likely to have significant difficulty in direct analysis. Objective identification of the particular sound, however, is suggested by the following known relationships: (1) the first group of vibrations of heart sound one HS I, coincides with either the "R wave" or the RS slope of the ECG, (2) the aortic components of heart sound two HS II, coincide with the end of the "T wave" of the ECG, (3) heart sound four, HS IV, (a diphasic or triphasic slow wave indicating presystole) falls at the end of the "P wave" and always precedes the Q wave and (4) abnormal vibrations (including opening snap, heart sound three) have no definite coincidence with the ECG. These relationships can be seen by a comparison of the ECG data of FIG. 1 with the (simultaneously generated) low frequency sound data of FIG. 2. Abnormal first and second sounds can indicate hypertension, mitral stenosis, bundle-branch block, myocarditis, aortic insufficiency, thyroid disease, diastolic and systolic overload and many other diseases. Abnormal third and fourth heart sounds are indicative of various hemodynamic disturbances such as heart murmurs. Thus, the accurate identification of heart sounds provides a diagnostic tool of broad range.

Presently two methods are commonly used for extraction of the useful data contained in heart sounds; (1) auscultation with the aid of a stethoscope and (2) phonocardiography. By far the most widely used of these methods is auscultation. Such analysis, however, is hampered by the limitations of the human ear. The normal ear is incapable of detecting many of the sounds produced by the action of the heart, resulting in a loss of information of diagnostic value. Additionally, the common stethoscope does not identify that portion of the heart cycle which is generating a particular sound. Such indeterminancy often results in the mis-identification of heart sound data and negates, or worse yet, results in inaccurate diagnosis of, the raw sound data.

Recognition of the useful data contained in heart sounds and of the above-described relationships has led to the development of phonocardiography. This art attempts to circumvent the inherent subjective difficulty in interpretation of heart sounds by the visual display of simultaneously generated sound and ECG data in the manner of FIGS. 1 and 2.

Present day phonocardiography is practiced by means of rather bulky systems containing both ECG and audio channels to monitor the heart's action. Typically, the data generated are displayed on strip chart recorders which provide the physician, generally a cardiologist, with a permanent, objective record of heart activity that utilizes the known relationship of heart sounds and ECG. The two "readings" are displayed on side-by-side graphs generated by the coaction of voltage-responsive styluses with a motor-driven roll of graph paper and diagnosis is made on the basis of the known temporal relationship of heart sounds and ECG. The styluses must be allowed freedom of movement which, along with the space required to house the chart drive motor and other mechanical components, serves to contribute to the bulkiness of the device. Additionally, the motor places a large power-consumption requirement upon the present-day phonocardiograph.

The phono data of the current phonocardiogram is displayed directly by the strip chart recorder when the low frequency data (approximately 80-100 Hz) are selected. Mid and high frequency data of the phonocardiogram are generated by the amplitude modulation of a carrier frequency. The carrier is necessarily of very low frequency with respect to a variety of significant heart sounds for compatibility with the electromechanical stylus. Preejection click, for example, is characterized by a fast, short wave (300-1000 Hz) which cannot be delineated effectively upon the 85 to 100 Hz carrier frequency generally employed. This disparity in frequencies occasioned by the electromechanical tracing of extremely high frequencies has led to the necessary application of envelope detection methods to the heart sounds prior to carrier modulation. These methods, which involve the smoothing of the high frequency waveform to accentuate the prominent components thereof, necessarily involves the use of filters and the selection of appropriate system time constants (attack, decay times) and such choices, in turn, incorporate tradeoffs whereby detail is sacrificed for the "overall picture".

In addition, the taking of a phonocardiograph by means of bulky, present day apparatus entails a complex patient "hook up" process that includes the attachment of a sensor having a diameter of approximately two (2) inches to the patient to detect the heart sounds and transform them into stylus-influencing electrical signals. The sensor, which attaches to the chest wall, obscures the area around the heart and prevents the physician from listening to the heart sounds as they are being recorded and displayed. To the general physician, unfamiliar with visual display of heart sound data, the absence of audio sensing of the heart sounds is often an uncomfortable experience until practice "weans" him away from his aural crutch.

SUMMARY OF THE INVENTION

This invention provides an improved method and compact apparatus for analyzing heart activity incorporating the principles of phonocardiography. Which involves the generation and processing of both analog and digital signals; the analog portion of the process is confined mainly to the (initial) waveshaping function while the digital portion, relating to the data presentation, imparts great flexibility in mode of display at a minimal system size and power requirement. The QRS signal is combined with the heart sound signal to produce an annotated heart sound signal which is displayed.

Proper medical analysis of the normal ECG requires a system capable of wideband operation including a frequency as low as 0.05 Hz. Group delay properties of filters at low frequencies result in large start-up times which can be as high as twenty seconds. Low frequency response is required when the chest piece is in use. Provision is made to sense an "in use" condition of the chestpiece to vary the bandpass region of filter/amplifiers which are employed to achieve quick turn-on operation.

BRIEF DESCRIPTION OF THE DRAWINGS

Referring now to the drawings in which like numerals represent like parts throughout:

FIG. 8a is a graph of the output of the high pass filter of the full screen ECG control circuit of the present invention;

FIGS. 8b and 8c, along with the accompanying text of the specification, describe the one-shot circuit timing processes utilized by the present invention to derive the annotation signal (shown in FIG. 8c);

DETAILED DESCRIPTION OF THE INVENTION

Figure 3:
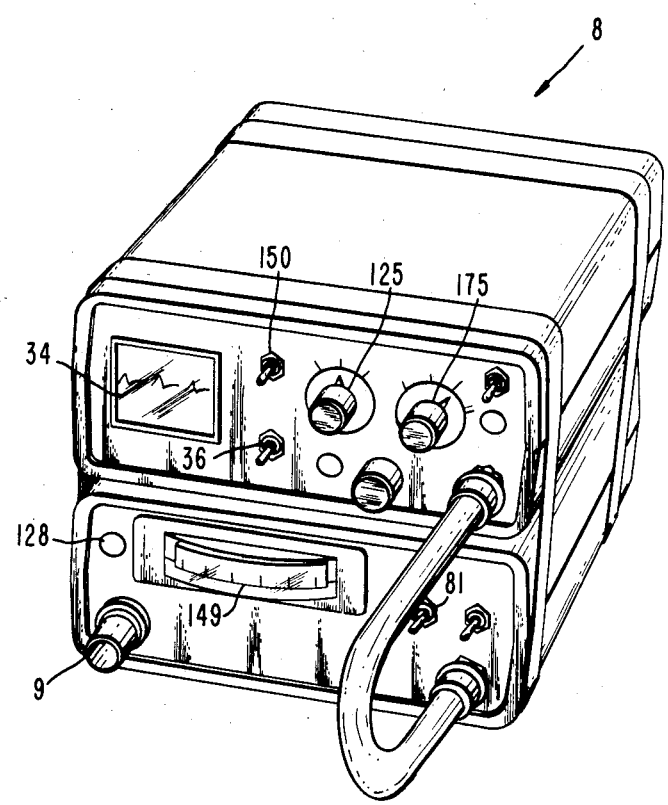
FIG. 3 is a view of the compact modular cardiac analysis device the present invention.
Figure 6:
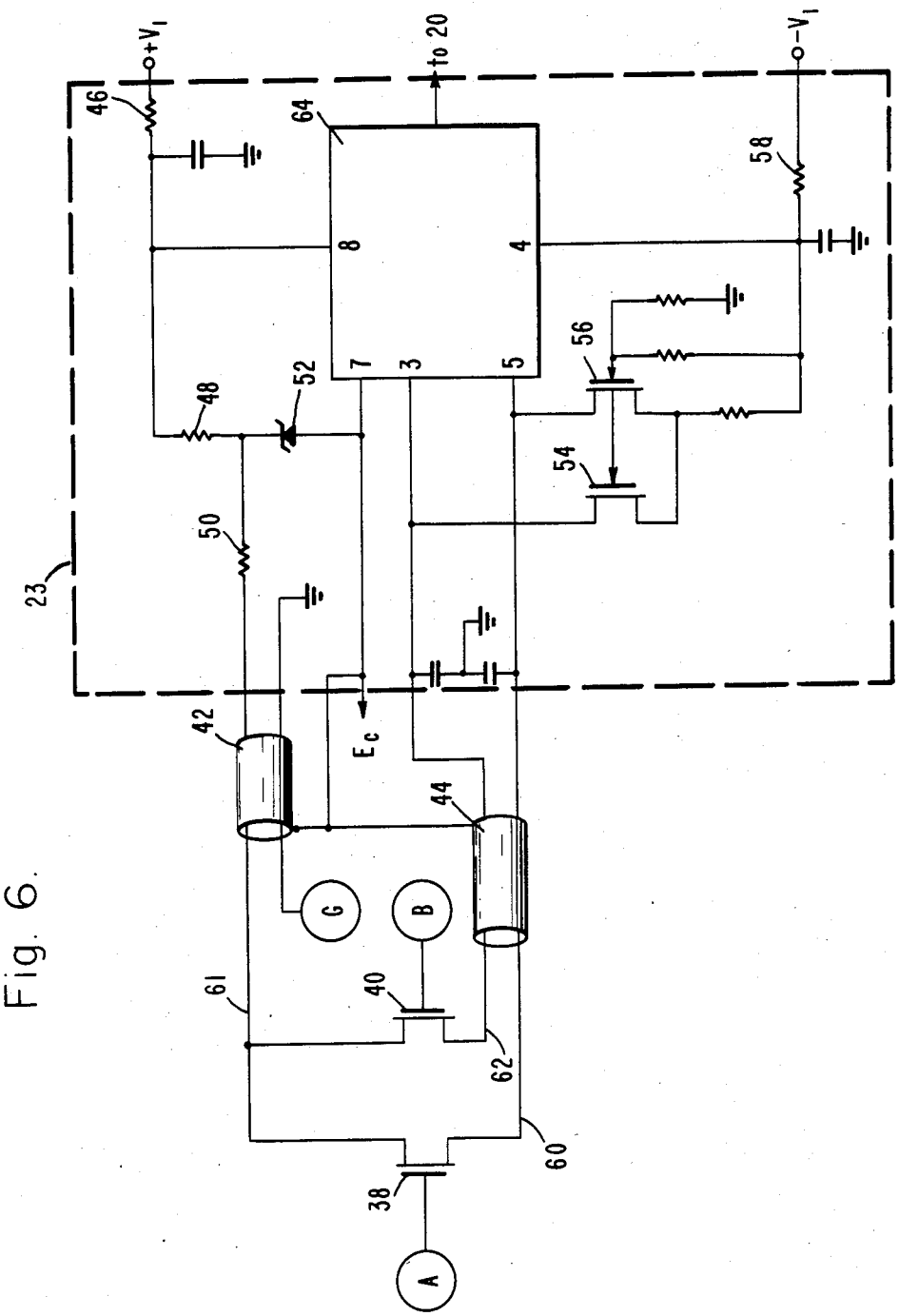
FIG. 6 is a diagram of the chestpiece pickup circuit of the present invention.

Referring now to the drawings, there is shown in FIG. 3 the compact modular cardiac analysis device 8 of the present invention. The device 8 comprises a lightweight, portable unit measuring $5\frac{1}{2} \times 6 \times 7\frac{1}{2}$ inches, presenting a drastic reduction in size over present day apparatus. The face or front panel of the device 8 includes, inter alia, a number of manual switches allowing the physican to avail himself of the multiple capabilities of the device. The significance and operation of each of these switches will be discussed, infra. The panel switches include a double pole ECG/Phono selector switch 36, an ECG bandwidth selector switch 81, a "Freeze or Run" switch 150, an adjustment switch 125 for the variable bandpass filter of the phono channel and a sweep rate adjustment control 175 which controls a write clock 174 (not shown). Display elements arranged on the face of the device include a CRT screen 34, a heart beat rate meter 149 and a "Chestpiece-in-Use"

indicating LED 128. An input port 9 is provided for hook-up of the electronics of a chestpiece 10 (FIG. 4a) to the device 8. The chestpiece 10, the ECG pick-up circuitry of which is disclosed in FIG. 6, is an electronic stethoscope chestpiece for picking up both heart sounds and analog electrical data corresponding thereto. Preferably, a plurality of ECG electrodes are mounted on the chestpiece 10 for the simultaneous detection of ECG data.

Figure 4A:
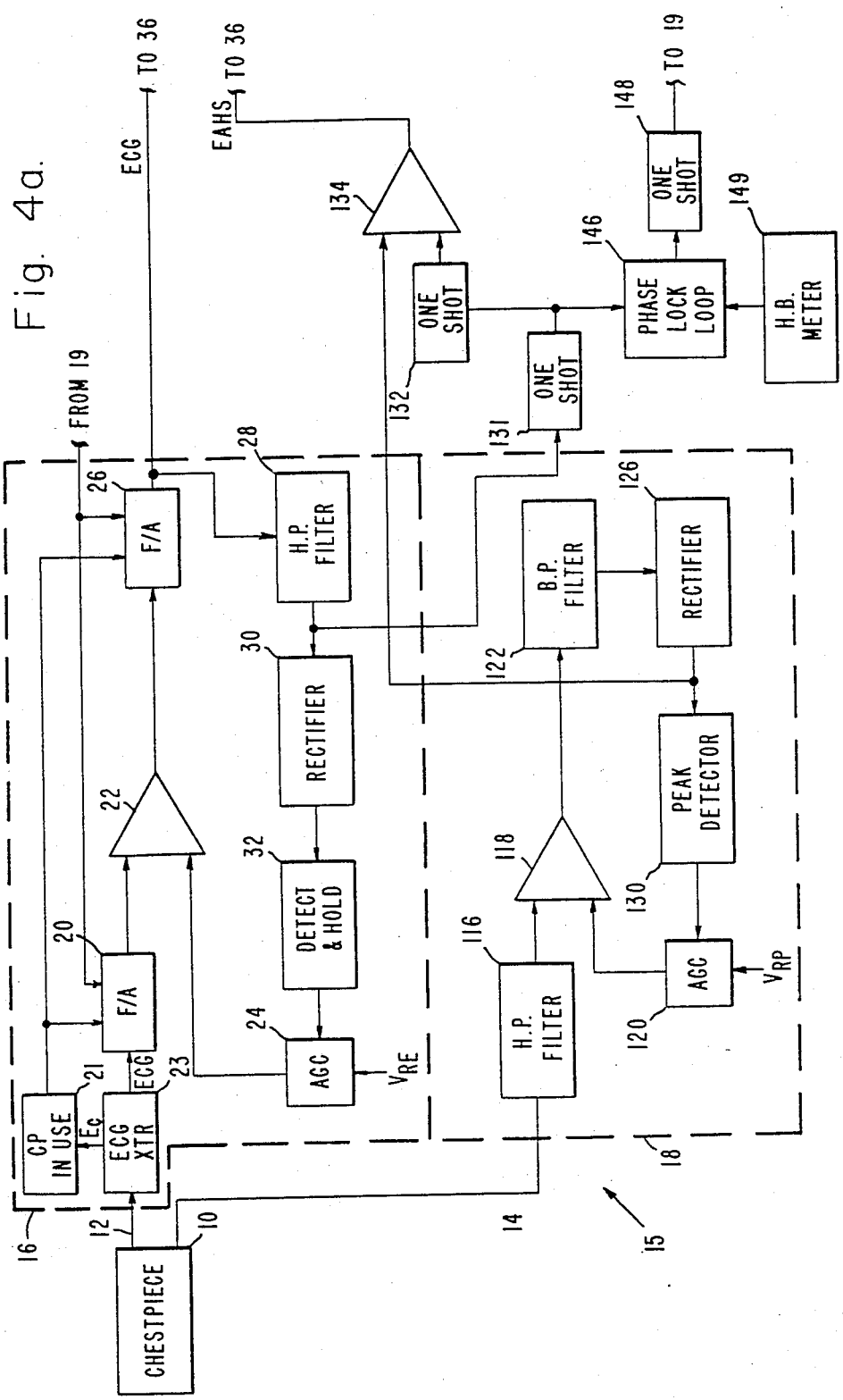
FIGS. 4a and 4b, taken together, present an overall circuit diagram of the system of the present invention.
Figure 4B:
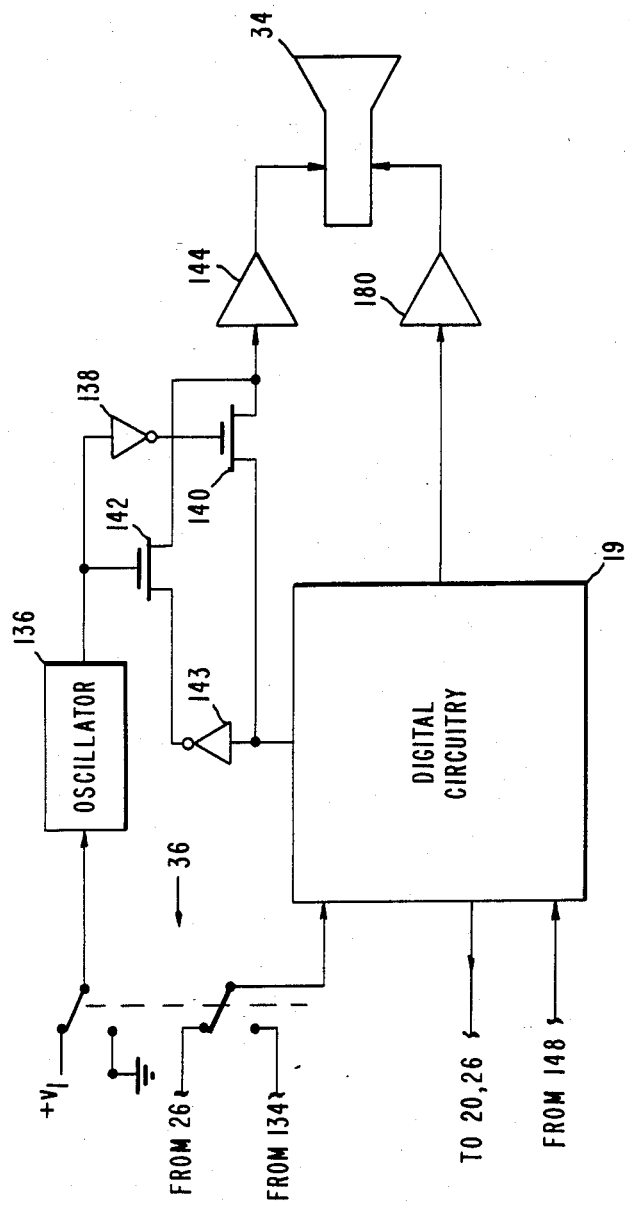

A block diagram of the overall system constituting the invention herein is shown in FIGS. 4a and 4b. The system receives patient data through the chest piece detector 10. Electrical inputs to the system include, of course, both the ECG voltages and voltages representing associated heart sounds. These analog voltages are directed through an ECG channel 12 and a phono channel 14, respectively, for individual amplification and processing. The processing of the data is in both instances achieved sequentially by means of analog wave shaping circuitry 15 (including both the full screen ECG control circuit 16 and the full screen phono control circuit 18) and digital data processing and display circuitry 19. The full screen control circuits 16, 18 are somewhat similar. However, due to the peculiarities of the ECG and heart sound signals processed therein and due, further, to the medical significance of particular characteristics of these signals, each of the circuits 16, 18 has been designed for and achieves a particularized operation.

FULL SCREEN CONTROL CIRCUITS

Figure 1:
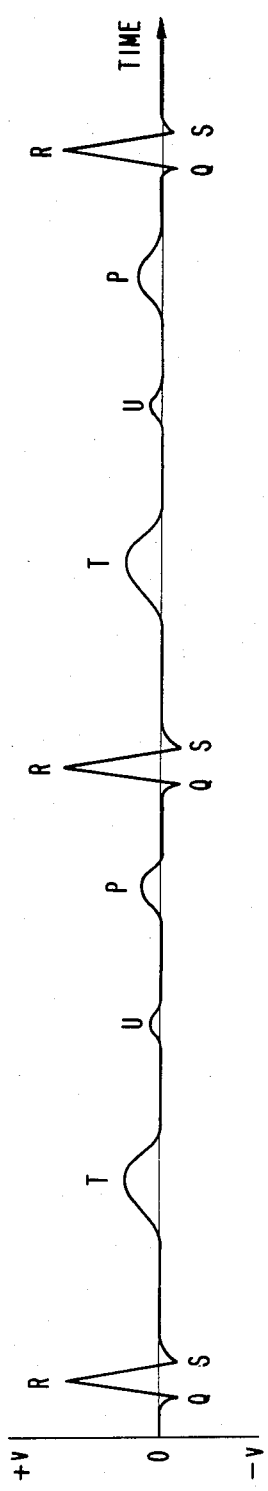
FIG. 1 is a graph of the electrocardiagram for a normal, at rest, human heart.
Figure 2:
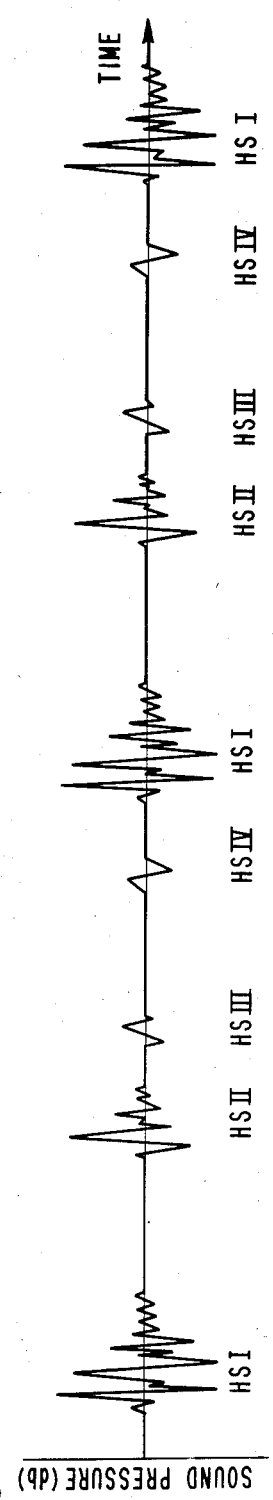
FIG. 2 is a graphic display of the heart sounds simultaneously produced by the normal, at rest, human heart.

With specific reference to the full screen ECG control circuit 16, the detected ECG signal (as displayed in FIG. 1), after chestpiece preamplification and preliminary noise filtering by an ECG extraction circuit 23, is applied to the bandpass. filter 20. The bandpass filter 20, which includes active elements, provides not only frequency rejection but also gain and, for such reason, is denominated a filter/amplifier. An operational device constructed according to the principles of the present invention included two pole (12 db/octave) filter/amplifiers 20 and 26. After the noise filtering and amplification by the filter/amplifier 20, the ECG signal is next applied to a variable amplifier 22, the gain of which is controlled by the output of a comparator 24. The variable gain amplifier 22 and the comparator/AGC control circuit 24 function as two elements of a servo loop which additionally includes the filter/amplifier bandpass filter 26, a high pass filter 28, a full wave rectifier 30 and a peak detect and hold circuit 32. Parameter values for the above-named elements as employed in a functioning device according to the present invention included a gain of two (2) and a bandpass range of 0.05 to 100 Hz for the (two pole) filter/amplifiers 20 and 26, an amplification range of 10 to 10,000 for the variable gain amplifier 22 and a cutoff frequency of 5 Hz for the (one pole) passive high pass filter 28.

The full screen ECG control circuit 16 has two principal functions. In the first instance, the circuit 16 provides a full screen (2 volts, peak-to-peak) ECG (that is the QRS complex fills one half of the CRT 34 vertical display area) and, in the second instance, the circuit 16 provides the basis for derivation of a "heart sound annotation signal" and a "zeroing" signal, the former allowing the physician to identify the displayed heart sound data with great certainty and the latter providing a control for the location of displayed data on the screen of the CRT 34. Regarding the first of the aforementioned functions of the circuit 16, a general discussion of the functioning of the servo loop disclosed above follows.

After the ECG signal is applied to the variable gain amplifier 22 and then filtered and amplified by the bandpass filter 26, a "good" (diagnostic quality) fullscreen ECG is obtained that is directed to one side of the channel selector switch 36. This same signal is fed back into the loop through the high pass filter 28 which strips the ECG of any existing low frequency drift. The high frequency peaks (particularly the QRS complexes) of the ECG waveform are passed by the filter 28 and applied to the full wave rectifier 30. The rectifier 30 prepares the signal for the conventional peak detect and hold circuit 32 which may include, for instance, an integrator with a diode in the feedback.

The peak detect and hold circuit 32 acquires and holds the amplitudes of the QRS complexes, such portions representing the maximum amplitudes of the ECG heart cycles, to produce a d.c. signal whose amplitude varies from one traverse of the loop to another (the time delay built into the comparator 24, discussed above, is somewhat slower, about four seconds, than the period of the typical heart cycle (about one second). Thus, only the QRS complex portion of the ECG is adjusted to full screen by the circuit 16. Other portions of the ECG signal are maintained in proportion thereto in terms of amplitude). This time-varying output is applied to the comparator/AGC circuit 24 wherein it is compared to a reference voltage VRE normalized for full screen CRT calibration. The resultant difference (or a function thereof) is then applied as the control voltage to the variable gain amplifier 22 which, in response, adjusts the amplitude of the QRS complex to one-half volt. Subsequent passage through the bandpass filter 26 amplifies this to one volt, producing an ECG signal such that the QRS segment occupies two-thirds of the height of the CRT screen. Thus, abnormally large, intermittent QRS signals are not clipped by the display and hence the term "full screen" in actual practice refers to two-thirds of the physical screen of the CRT 34.

Proper medical analysis of the normal ECG dictates the above-mentioned wideband operation of the circuit 16 including a relatively low frequency (0.05 Hz) range. The practical operation of the filter/amplifiers 20,26 in this range (significant to medical slow (P, T) wave analysis) is hindered by large start-up times occasioned by the unfavorable group delay properties of filters at low frequencies. The times required for the filters 20, 26 to achieve steady state frequency responses are proportional to the inverse of the filter/amplifier low frequency cutoff and thus can run as high as twenty seconds in this range. A delay of such magnitude removes a device of the nature herein (as opposed to the strip chart type device which produces a continuous readout wherein twenty seconds is not critical) from the realm of usable medical instrumentation. For this reason, the inventors have devised and employ in the system filter/amplifiers 20,26 and associated circuitry (disclosed in FIGS. 5, 6 and 7) which sense an "in use" condition and vary the bandpass region of the filter/amplifiers 20, 26 to achieve "quick" turn on operation. The mechanisms for this operation are discussed later.

"DRY" ECG ELECTRODES

FIG. 6 shows the ECG pickup circuitry (including the ECG extraction circuit 23) of the present invention. The numerals A, B and G denote, respectively, the first and second "measuring" ECG electrodes and the ground ECG electrode. The three electrodes are mounted in equally spaced circumferential positions on the rim of the chestpiece 10 in which the microphone 43, for picking up heart sounds, is centrally mounted. The first two electrodes provide spatially diverse measurements of electro-cardiac activity. The measuring signals detected by electrodes A and B are applied as gate voltages to a pair of high input impedance (low transconductivity) FETs 38, 40. The applicants have found that the use of a high impedance pickup allows the direct unbuffered application of all electrodes to the skin of the patient. In conventional ECG pickup devices a gel is applied to the skin for the purpose of providing a uniform electrical interface between the metal electrode and the skin. This gel generally contains a large concentration of ions, the purpose of which is to minimize electrochemical effects at the skin/metal interface. The flow of current through the electrode/skin interface and gel, however, alters the d.c. electrochemical potential of the interface. This alteration produces many undesirable effects including, in the instance of strip chart recording, the periodical running of the stylus off the paper recording strip to incapacitate the recording instrument. Applicants' use of the high input impedance FETS 38, 40 for signal pickup thus avoids, to a first order, the drift attendant upon the aforementioned electrochemical potential changes by minimizing the flow of current.

The high input impedances of the FETS 38, 40, about $10^{14}$ ohms (typical present day ECG device input impedances range from $10^6$ to $10^7$ ohms. The present invention utilizes an input impedance which is one to ten million times as large), are coupled with relatively low output impedances (lower by a factor of about $10^6$). This impedance differential can be achieved by Applicants' use of FETs commerically available as Device Package U423 from Siliconix, Inc. of Santa Clara, Calif. The use of such FETs dictates the placement of the FETs close to the electrodes in contact with the patient. As aforesaid, the high impedances of the FETs 38, 40 minimize signal drift by minimizing induced electrochemical effects at the skin/metal interface. Their relatively low output impedances minimize the noise content of the signals transmitted along the conductors 60, 61 and 62 and shielded cables 42 and 44. Thus, Applicants mount the detector FETs 38, 40 in (at the rim of) the chestpiece 10. The physical location of the remainder of the electronics shown in FIG. 6 (i.e., the ECG extraction circuit 23) is not critical and may be located according to convenience and design choices.

The circuitry of the ECG extraction circuit 23 includes current limiting resistors 46, 48 and 50 which minimize the current and a Zener diode 52 which limits the chestpiece voltage (to about 3 volts) resulting from the power supply $+V_1$ in consideration of the environment of use (i.e. the patient). A pair of FETs 54, 56, associated passive circuitry, and a current limiting resistor 58 protect the patient from the negative power supply $-V_1$. The last-named circuitry additionally provides a gain matching function with respect to the signals transmitted along the conductors 60, 62 (occasioned by the voltages sensed by the electrodes A and B) and the differential instrumentation amplifier 64. A suitable amplifier 64 is commercially available as part number 284 from Analog Devices of Norwood, Mass. The amplifier 64 functions to amplify the incoming noisy ECG signal and extract the "common mode" voltage, $E_c$ from the highly noisy signals carried on the conductors 60, 62. The common mode voltage is composed of various noise components including the 60 cycle electrical environment of the patient and the electrochemical effects of the skin/electrode interface. The voltage $E_c$ acts as an indirect control voltage for the filter/amplifiers 20, 26 and is a conventional shield driver for the cables 42, 44.

FILTER/AMPLIFIERS AND ASSOCIATED CIRCUITRY.

Figure 5:
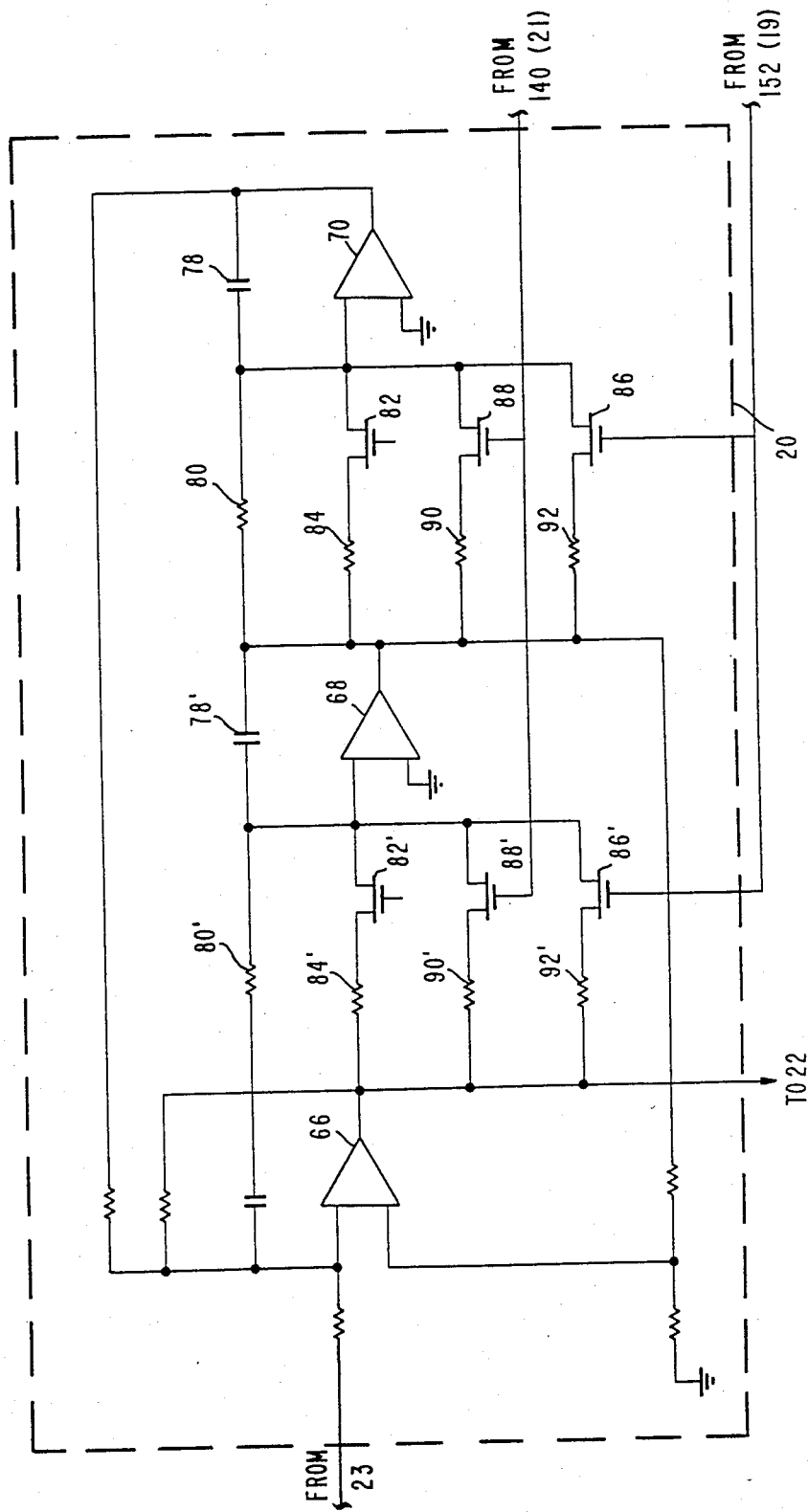
FIG. 5 is a detailed circuit diagram of the automatic filter/amplifiers utilized by the present invention.

The common mode voltage provides the system of the present invention with an indication of the physicians usage of the chestpiece 10 on a patient. As mentioned, supra, the medical necessity for ECG slow wave response introduces "turn on time" problems (group delay characteristics) with regard to the filter/amplifiers 20, 26. The invention herein overcomes this problem by means of the circuitry illustrated in FIG. 5 in conjunction with the control circuitry of FIG. 7. In FIG. 5, there is illustrated in detail the circuitry of the filter/amplifier 20. The filter/amplifiers 20 and 26 are basically identical, each comprising a three-operational-amplifier stage device having a variable-impedance feedback path. The filter/amplifiers 20, 26 are, in a sense, always "on". That is, when the common mode voltage, $E_c$, indicates that the chestpiece 10 is not in use, they remain responsive to a range of frequencies which does not entail a large turnon time (i.e. the lowest frequency is considerably above 0.05 Hz). When actual medical use is being made of the chestpiece 10, the bandwidth of the system is switched to include responses in lower frequency bands so that the desired frequency response is obtained without a concomitant, large turn-on time.

Referring now to FIG. 5, the filter/amplifier 20 is seen to comprise three cascaded feedback amplifier stages having selectable and variable input impedances. The operational amplifiers 66, 68, 70 comprise the active circuitry of the filter/amplifier 20. The high frequency response of the filter/amplifier is limited to 100 Hz by the RC feedback associated with the amplifier 66. The low frequency response is limited by the combined effects of the two pole active filters or operational amplifiers 68, 70. The low frequency "roll-off" point of the filter/amplifier 20 is determined by the combined effects of feedback impedances including the capacitors 78, 78', the resistors 80, 80' and various additional, selectable resistances introduced thereto through the action of a variety of switching FETs (to be discussed). Referring to the third stage of the filter/amplifier 20, the "basic" frequency-dependent gain characteristic of the operational amplifier 70 is influenced by the capacitor 78 and the resistor 80, the values of which are selected for a frequency response (with chestpiece 10 "on" or "in use") of 0.05 to 100 Hz. (The front panel switch 81 controls the FETs 82, 82' which, when "on", put the resistors 84, 84' into the feedback paths. When selected for any of a number of medical diagnostic reasons-generally relating to noise-the bandwith of the filter/amplifier 20 is altered to a range of 0.5 to 100 Hz.) The FETs 86, 86' switch the resistors 92, 92' into the impedance network within the filter/amplifier 20. Such switching is responsive to a pulse occurring at the beginning of CRT raster sweep. Upon receipt of this pulse and the attendant switching of the resistors 92, 92' into the impedance network, a relatively narrow filter/amplifier bandwidth of, for example, 50-100 Hz is produced. This narrow frequency range eliminates the low frequency "d.c. drift" acquired by the operational amplifiers 66, 68, 70 during the prior raster sweep—in effect "zeroing" the filter/amplifier 20. The result of this repeated zeroing is the return of the baseline of the ECG electrical signal to mid-screen of the CRT 34 after an appropriate settling time 0.020 seconds for a lower bound of 50 Hz). The FETs 88, 88' switch the resistors 90, 90' into and out of the network. The state of these FETs (conductive or not) is responsive to the detection of one second of uninterrupted contact between the chestpiece 10 and patient (The apparatus for detection of contact and the resultant signal generated will be discussed in the description of the circuitry shown in FIG. 7.) In the present invention, a high voltage (logical "one") level is applied to their gates from the circuitry of FIG. 7 when the chestpiece 10 is not in use (i.e., not in contact with a patient). This voltage level goes low (logical "zero") when uninterrupted contact is detected, removing the resistors 90, 90' from the impedance network, the result of which is a filter/amplifier 20 bandwidth range of either 0.05 to 100 Hz (FETs 82, 82' "off") or 0.5 to 100 (FETs 82, 82' "on") depending upon the manual setting of the front panel switch 81. Summarizing, the following table presents the bandwidths achieved by the filter/amplifiers 20, 26 by means of the circuitry shown in FIG. 5:

| Gate High - FET | Bandwidth |
| --- | --- |
| — | .05–100 Hz |
| 82, 82' | .5–100 Hz |
| 88, 88' | 5–100 Hz |
| 86, 86' | 50–100 Hz |

The above bandwidths were achieved in the practice of the present invention by means of cascaded stages, such as the above-described, employing TL 062 operational amplifiers manufactured by the National Semiconductor Company of Carpenteria, Calif. in conjunction with the following resistor values:

| Resistor | Resistance Value |
| --- | --- |
| 80 | 32 Megohms |
| 84, 84' | 3.3 Megohms |
| 90, 90' | 316 Kilohms |
| 92, 92' | 22 Kilohms |

Thus, the filter/amplifiers 20, 26 have a bandwidth range of 5–100 Hz when the chestpiece 10 is not in use (i.e., not in contact with patient's chest). The 5 Hz low frequency boundary is not subject to the twenty second period of 0.05 Hz but rather requires 0.2 seconds after the occurrence of a signal transient (such as that which occurs when the chestpiece 10 is applied to the patient) for full responsiveness throughout this bandwidth.

Figure 7:
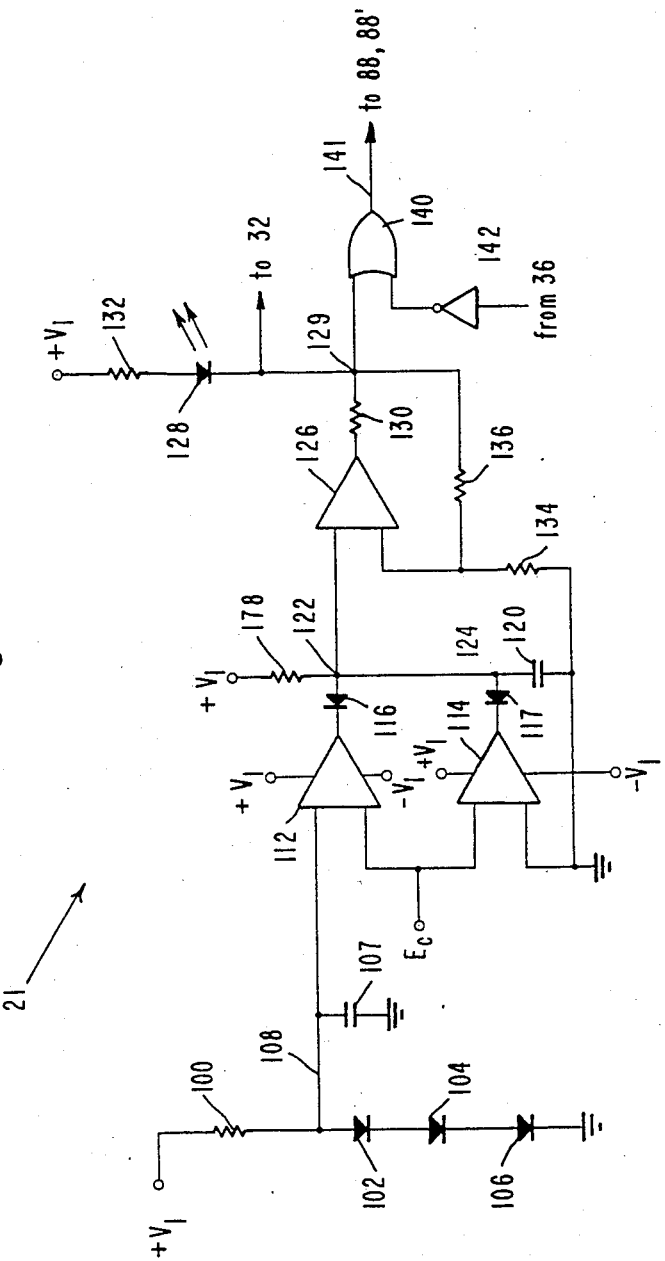
FIG. 7 is a diagram of the filter/amplifier control circuit utilized in the present invention.

Referring now to FIG. 7, there is illustrated in detail the "Chestpiece-in-Use" detector circuit 21 by means of which the bandwidths of the filter/amplifiers 20, 26 are automatically switched from 5 to 100 Hz to either 0.05 to 100 Hz or 0.5 to 100 Hz (dependent upon the state of the FETs 82, 82') when the chestpiece 10 is in use. The circuit 21 produces and applies (via a conductor 141) a bandwidth-controlling signal to the gates of the low frequency threshold shifting FETs 88, 88' of the filter/amplifier 20 (and to the corresponding FET's of the filter/amplifier 26). The behavior of $E_c$ provides the control criterion for the bandwidth determination. The inventors have found (by experimentation) that the electrical potentials observed between dry metal electrodes in contact with the skin can vary as much as ±0.6 volts due to electrochemical effects at the metal/skin interface. Thus, a common mode signal, $E_c$, of as much as ±0.6 volts can be observed between the measuring electrodes, A and B and the ground electrode G when the chestpiece containing the electrodes is in contact with the patient. In addition to this ±0.6 volt potential swing, there exists a +0.7 volt dc common mode signal resulting from the gate-to-drain offset voltage of the preamplifier FET's 38, 40 of the chestpiece 10. Therefore, when the chestpiece 10 is in contact with the skin of the patient, the common mode signal, $E_c$, lies between +0.1 volts (+0.7−0.6) and +1.3 volts (+0.7+0.6). When the electrodes are *not* in contact with the skin of the patient, omnipresent stray electrical fields cause the chestpiece preamp FETs 38, 40 to saturate as a result of their extremely high input impedances. The saturation, in turn, causes $E_c$ to (1) saturate at either +3 volts (this is the limit set by the Zener diode 52) or (2) oscillate between these levels at the frequency of the spurious electrical fields (typically 60 Hz).

Based upon the aforementioned, the inventors have designed and contructed the "Chestpiece-In-Use Detector Circuit" of FIG. 7 which senses the value of $E_c$ and provides a signal that selects the appropriate low-frequency boundary for the filter/amplifiers 20, 26 in accordance therewith.

CHESTPIECE-IN-USE DETECTOR CIRCUIT

Referring now to FIG. 7, a preselected reference voltage (1.5 volts) is established along the equipotential voltage rail 108 by the imposition of a voltage $V_1$ on the combination of the diodes 102, 104, 106 and the power limiting resistor 100. The operational amplifiers 112, 114 are connected to form an $E_c$ window comparator which operates between the reference voltage of +1.5 and zero volts. The range of 0–1.5 volts (as opposed to 0.1 to 1.3 volts) makes allowance for the small ECG voltage which rides on the $E_c$ signal. When $E_c$ falls without the range of 0–1.5 volts, a circuit node 122 is pulled to $-V_1$, the value of the negative power supply to the comparator 112. This occurs, for example, when $E_c$ is "too high" (FETs 38, 40 saturated at +3 v). In such case the output of the operational amplifier 112 is $-V_1$ in response to $E_c$ exceeding the positive reference input. This voltage level turns the diode 116 on so that current flows from $+V_1$ through the resistor 178 and amplifier 112. The output of the operational amplifier 114 is maintained at $+V_1$, (the result of a positive comparison between the terminals of the amplifier 114) as the diode prevents the passage of current from the amplifier 114 to the node 124; thus, all flow of current through the node 122 is sunk through the operational amplifier 112. As the forward resistance of the diode 116 is quite low (about 0.5 volts), the voltage divider formed by the diode 116 and the resistor 178 apportions the voltage drops therein so that the potential at the node 122 is nearly identical to the voltage output of the operational amplifier 112. Analogous behavior occurs with regard to the operational amplifier 114 when $E_c$ falls outside the aforementioned voltage window at the low (e.g. −3 volts) end of the range. Thus, in either instance, a voltage of about $-V_1$ is applied to the minus input of the amplifier 126. When the node 122 is low, (i.e. at $-V_1$), the output of the window detector operational amplifier 126 goes high, raising the potential at the node 129. The high potential at the node 129 inhibits the luminance of the LED 128 and additionally drives the output of the OR gate 140 high. The high output of the OR gate 140 is, in turn, distributed to the aforementioned FET switches 88, 88' (FIG. 5) by the conductor 141, turning them "on" and setting the low frequency response of amplifier/filters 20, 26 to 5 Hz which, as discussed supra, corresponds to the idling or "Not In-Use" state of the chestpiece 10.

When the chestpiece mounted electrodes, A, B and G are in contact with the patient, $E_c$ falls within the range of 0.1 to 1.3 volts as the chestpiece FET's are no longer saturated and are within the window range of the comparator comprising the operational amplifiers 112, 114. In such instance, the output of the operational amplifier that had been holding the corresponding circuit node near $-V_1$ at the time prior to contact is thereby changed to $+V_1$. As a result, the series diode is rendered nonconductive. The voltage at the node 122 will begin to rise as the current through the resistor 178 charges a capacitor 120. When the voltage rises at the node to a preselected level, (determined by the values of the resistors 132, 134 and 136) the output of the window detector operational amplifier 126 goes low. The time required to charge the capacitor 120 through the resistor 178 in an actual embodiment of the present invention was chosen to be one second. The incorporation of such time delay insures the correct recognition of an "In-Use" condition in that spurious incursions into the voltage window by $E_c$ will not trigger the circuit. $E_c$ must remain within the voltage window for one full second: if $E_c$ wanders outside the window, even momentarily, during the one second charging time of the capacitor 120, the voltage at the circuit node 122 resets to $-V_1$. When the one second approval condition has been satisfied, the circuit node 129 goes low. The low potential at the node 129 causes the LED 128, which may be mounted on the instrument's front panel (as in FIG. 3) or on the chestpiece 10, to light up, indicating that good electrical contact has been made to the patient. The low state at the node 129 is applied to the OR gate 140 along with the (inverted) output of the manually operable Phono/ECG selector switch 36. The selector switch 36, when set at "Phono" by the physician, provides a high or logic "one" input to the OR gate 140. This high or logic "one" is transferred to the output of the OR gate 140 for transmission to the FET's 88, 88' (and corresponding FET's of the filter/amplifier 26), maintaining the low frequency response of amplifier/filters 20, 26 at 5 Hz. When the switch 36 is set to "ECG", a low state is applied to the OR gate 140. This input, coupled with the low state that exists at the circuit node 129 when $E_c$ falls within the aforesaid "window", drives the output of the OR gate 140 low (logic "zero"). This low output state alters or drives the low frequency responses of the filter/amplifiers 20, 26 to 0.05 Hz or 0.5 Hz as aforementioned. The table below summarizes the operation of the In-Use-Detector circuit 21.

From the above discussion and table it can be seen that the circuitry of FIG. 7 does indeed switch the filter/amplifiers 20, 26 to a lower bandwidth range upon the detection of one second of uninterrupted contact between the chestpiece 10 and the body of a patient. As a result of the aforementioned (and assuming that the ECG rather than the phono mode has been chosen by the listener), shifting of the lower bound of the bandwidth takes place automatically so that the inherent time delay for the practicing physician is one second (time required to determine that the chestpiece 10 is "on") rather than, for instance, twenty seconds (0.05 Hz start up time).

Returning now to the overall system as illustrated in FIG. 4, it can be seen that the phono channel 14 applies the audio data acquired by the chestpiece 10 to the full screen audio control circuit 18, which, although similar to the full screen ECG control circuit 16, comprises a simpler control loop. The simplicity of the full screen audio control circuit 18 in comparison to the full screen ECG control circuit 16 (which is reflected in the absence of automatic bandwidth-switching filter/amplifiers as described, supra) is due, in large part, to the higher low frequency (audio) passband processed by the circuit 18. The phono signal containing analog audio data is first applied to a high pass filter 116 which strips the signal of any d.c. component and of low frequency noise. The filtered signal is next applied to a variable gain amplifier 118, the gain of which is controlled by the comparator/AGC circuit 120. The output of the variable amplifier 118 (in an operational model of the present invention, a range of 3 to 1,000 was employed for the adjustable gain of the amplifier 118) is next applied as an input to the three-range bandpass filter 121. The three frequency ranges of the filter 121 include (1) the low frequency only band (10–100 Hz) (2) the high frequency only band (100 Hz–1000 Hz) and (3) the entire bandpass (10–1000 Hz). Any one of these three frequency bands may be selected by the physician turning the front panel selector switch 124. The physician selects the bandpass according to the type of medical analysis desired; that is, a particular heart sound of interest (lying in a defined frequency range) may be "zeroed in" and/or the physician may select a view illustrating a number of the heart sounds (wideband operation) for cardiac analysis. The output of the filter 122 is then applied to the full wave rectifier 126. The rectifier 126 produces a positive-going waveform in the desired heart sound frequency bandwidth. This rectified analog (phono) signal is then applied to a summing amplifier 134. The summing amplifier 134 combines an annotation signal (discussed infra) with the phono signal to produce a rectified "ECG Annotated Heart Sound (EAHS)", a medically significant form of data by which the simultaneously generated audio data and ECG data of the heart may be correlated. The rectified audio data is additionally applied to the peak detector circuit 130 which functions in a manner similar to the peak detect and hold circuit 32 of the full screen ECG circuit 16.

TABLE 1

| $E_c$ | Output of 112 | Output of 114 | Node 122 | Node 129 | Switch 36 | OR gate 140 | Low Freq. Resp. of 20 and 26 |
|---|---|---|---|---|---|---|---|
| Too High | Low | High | Low | High | — | High | 5 Hz |
| Too Low | High | Low | Low | High | — | High | 5 Hz |
| In Range | High | High | High | Low | Phono ECG | High Low | 5 Hz .05 Hz/.5 HZ |

The output of the peak detector 130, a signal whose amplitude is proportional to the largest amplitude heart sound in the bandwidth selected by the physician (via manual switch 124) is then applied to the aforementioned AGC control/comparator circuit 120. The output of the circuit 120 is a voltage whose magnitude is a function of the output of the peak detector 130 and a reference voltage $V_{RP}$ indicative of a normalized (one-half screen, peak-to-peak) amplitude for the phono signal. Thus, the comparator 120 applies a control signal to the variable gain amplifier 118, adjusting its gain so that the amplitude of the output of the full wave rectifier 126 is a voltage that corresponds to the peak value, filling one half of the screen of the CRT 34.

Summarizing, it can be seen that three output signals are generated and/or, shaped, by the electronics of the analog wave shaping circuitry 15. (The relevance of these signals will become apparent in the discussion of the digital processing and display circuitry 19.) These signals are (1) a diagnostic quality full screen ECG signal, the output of the bandpass filter 26 of the full screen ECG control circuit 16, (2) a timing signal, the output of the high pass filter 28 of the circuit 16, and (3) a rectified, one-half full screen phono signal, the output of the rectifier 126 of the full screen audio control circuit 18.

ANNOTATION SIGNAL

Figure 8D:
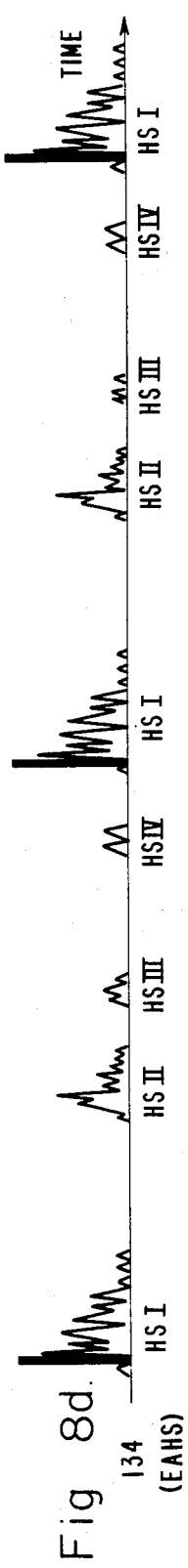
FIG. 8d displays the annotation signal superimposed upon the rectified heart sounds signal.

A heart sound annotation signal (HSA) is generated from the QRS complexes of the ECG data. The annotation, generated simultaneously with the phono data, serves to locate the various heart sounds when superimposed thereon, thereby providing an objective tool for the analysis of heart sounds. Referring to FIG. 8a, there is illustrated the ECG signal of FIG. 1 as emergent from the high pass filter 26. The signal displayed contains essentially no low frequency perturbations, consisting mainly of the QRS complexes of the ECG's with heart cycle spacing. The filtered ECG signal of FIG. 8a is applied to a one shot 131 having a relatively wide (on the order of 300 milliseconds) pulse width. Each pulse output of the one shot 131, as illustrated in FIG. 8b, is considerably less than one heart cycle in duration and serves to identify or locate the QRS complex of the corresponding heart cycle. The output of the one shot 131 is next applied to an additional one shot 132 having a considerably narrower (on the order of 30 milliseconds) pulse width than that of the one shot 131. This pulse, which is illustrated in FIG. 8c, is the rectified heart sound annotation (HSA) signal and is superimposed upon the full scale rectified phono signal (output of the rectifier 126 of the full scale audio control circuit 18) by means of the summing amplifier 134 to produce the rectified EAHS signal. The rectified EAHS signal, illustrated in FIG. 8d, consists of the annotation superimposed upon rectified phono data in the bandwidth of interest (chosen by the physician's setting of the switch 124). As can be seen in FIG. 8d, the superposition of the annotation upon the heart sound data is extremely useful, for example, in distinguishing the H.S. III data from the H.S. IV data and the H.S. I data from the H.S. II data. The EAHS and the diagnostic quality ECG output of the filter/amplifier 26 comprise the inputs to the (two position) channel selection switch 36. Reserving for later discussion the intermediate digital signal processing of the digital encoding and associated display circuitry of the invention, one may see that, by positioning the switch 36, the physician can elect to display either the ECG data or the audio data annotated by the QRS complex of the ECG (EAHS).

"SYMMETRIZING" OF PHONO DATA

Figure 8E:
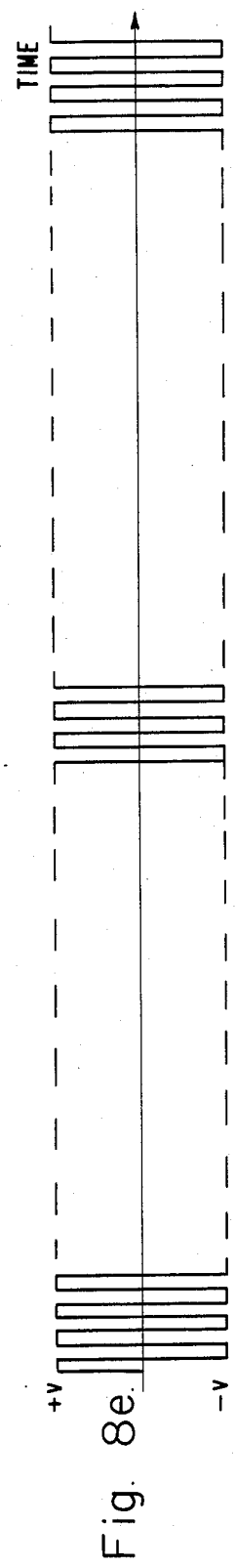
FIG. 8e discloses the output of the chopping oscillator which is utilized to "symmetrize" the signal data of FIG. 8d.
Figure 8F:
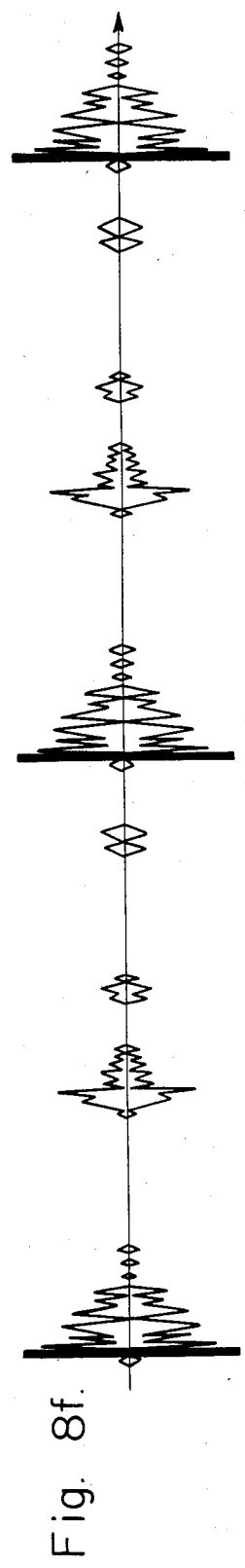
FIG. 8f shows the ECG annotated heart sound signal (EAHS) derived by the present invention.

When the physician selects the "annotated phono" position of the switch 36, the analog annotated phono data (EAHS signal), as illustrated in FIG. 8d, is applied to the digital processing circuitry 19, and the chopping oscillator 136 activated. The oscillator 136 produces the function illustrated in FIG. 8e which is characterized by alternating periods of positive voltage $+V$ and negative voltage $-V$. The interposition of the inverter 138 between the gate of the FET 140 and the chopping oscillator 136 inverts the control signal applied to the gate of the FET 140 and that applied to the gate of the FET 142 to occasion the alternating switching "on" of the FETs 140, 142 to "symmetrize" the EAHS signal of FIG. 8d as emergent, after processing (discussed infra), from the digital circuitry 19. That is, the rectified, annotated data illustrated as the EAHS signal in FIG. 8d is reconstituted to analog form after processing in the digital display circuitry 19 (to undergo analog-to-digital-to analog conversion steps, discussed infra). The data representative of the vertical displacement of the EAHS signal emerges from the circuitry 19 and is applied directly to the source of the FET 140 and, after inversion, to the source of the FET 142. The frequency of the oscillator 136 is sufficient, on the order of 10 kHz, so that the resultant signal applied to the vertical deflection amplifier 144 will resemble the graph of FIG. 8f and the image may be thereby presented without observable flicker on the screen of the CRT 34. In the event that the front panel selector switch 36 is positioned to pass the ECG signal to the digital processing circuitry 19, the chopping oscillator 136 provides a negative-going constant voltage whereby just one of the two FETs (the FET 140 in the event of an N-channel device) conducts so that the above-described "symmetrizing" operation is not undertaken. By "symmetrizing" the EAHS data to derive the annotated phono signal, the present invention achieves a depiction of the heart sounds which surpasses in detail that obtainable by present day amplitude modulated phonocardiographs which utilize envelope detection of the heart sound signal. The "symmetrized" heart sound data shown in FIG. 8f is additionally beneficial to the physician in that this view coincides, in a general sense, with well-known shorthand medical notation for heart sounds.

DIGITAL DISPLAY CIRCUITRY

As seen in FIG. 4b, the digital display circuitry 19 enables the present invention to display the ECG and annotated heart sound (EAHS) data in a variety of analog modes. More particularly, the digital circuitry 19 processes the aforesaid incoming analog data generated by the analog front end wave-shaping circuitry 15 prior to application to the symmetrizing circuitry (comprising the oscillator 136, the inverters 138, 143, and the FETs 140, 142) and the horizontal and vertical deflection amplifiers 180, 144 which control the resulting image on the screen of the CRT 34. The resulting diagnostic quality ECG and symmetrized EAHS (of FIG. 8f) may then be selectively viewed by the physician (in accordance with the setting of the front panel switch 36). In addition, the digital circuitry 19 processes and transmits to the aforementioned FETs 86, 86[1] of the filter/amplifier 20 (FIG. 5) (and the corresponding FETs of the filter/amplifier 26) a signal or stream of pulses, each of which coincides with the completion of one full detected heart cycle. As mentioned above in connection with the detailed description of the operation of the filter/amplifiers 20, 26, this stream of "zeroing" pulses serves to shift the filter/amplifiers momentarily to a narrow bandwidth having a relatively high lower frequency bound (about 50 Hz) which removes any dc drift which the prior ECG cycle may have acquired, the net result of which will be the maintenance of the ECG signal, as eventually displayed on the screen of the CRT 34, close to mid-screen by cleansing the filter/amplifiers of dc drift acquired during each heart cycle. It will be seen that this "zeroing" signal, occurring at the end of one heart cycle, is utilized by the digital circuitry 19 for a number of additional purposes which take advantage of its quality as a "timing" signal.

Figure 9:
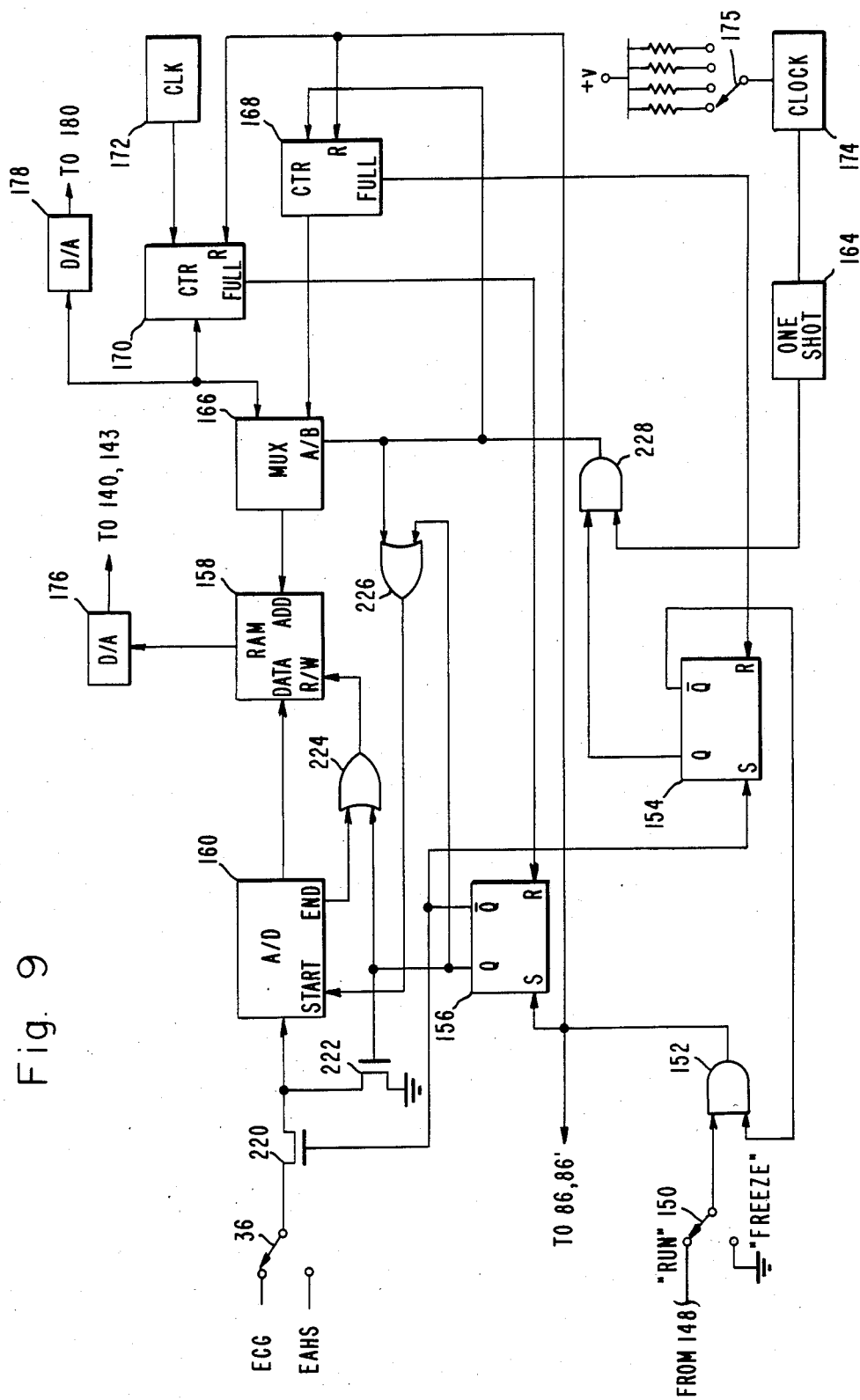
FIG. 9 is a detailed schematic view of the digital processing circuitry of the present invention.

Viewing the digital circuitry of FIG. 9 in greater detail, one may make a rough grouping of the elements thereof into "control" elements and "display" elements. Although this grouping is not exclusive and is by no means the only way to look at the digital circuitry 19, it will be convenient for analysis. The control elements accept inputs and commands from the system and interact to generate various control signals which direct the operation of the display elements. The control elements include AND gates 152, 228, OR gates 224, 226, a frame clearing flip-flop 156, and a data acquisition flip-flop 154. Display elements include FETs 220, 222, an analog-to-digital converter 160, a random access memory (RAM) 158, a multiplexer 166, a read counter 170, a write counter 168, a read clock 172, a variable rate write clock 174, a pulse narrowing one-shot 164, a vertical digital-to-analog converter 176 and a horizontal digital-to-analog converter 178.

The user, by setting various front panel switches shown in FIG. 3, is provided three degrees of freedom with respect to the operation of the digital circuitry 19 of FIG. 9. By choosing one of the two possible settings of the "Freeze or Run" switch 150 (enabling or inhibiting the AND gate 152), he selects either a "quasi-continuous" (continual updating of detected data, frame-by-frame) or a "freeze frame" display of the data on the screen of the CRT 34. As shown in FIG. 9, the switch 150 has been moved to the "run" setting so that the AND gate 152 receives periodic pulses from the one-shot 148 (FIG. 4a) which, as described above, coincide with the mid-QRS portions of the ECG cycle.

By manually setting the front panel switch 36, the user elects to display either the ECG or EAHS data. As mentioned above, in the event that the EAHS switch position (from the summing amplifier 134) is selected, the chopping oscillator 136 is activated so that, after the intermediate signal processing (to be described) within the digital circuitry 19, the EAHS data is symmetrized (i.e., the rectified signal of FIG. 8d is converted to that of FIG. 8f). In the event the ECG switch position is chosen, a diagnostic quality ECG (from the filter/amplifier 26) is passed to the vertical deflection amplifier 144 without symmetrization as the chopping oscillator 136 is not activated.

Finally, the user may select a desired data acquisition rate by positioning the front panel switch 175. This switch, which varies the rate of the write clock 174, alters the frequency of the pulse stream eventually applied to the write counter 168 so that the number of data points acquired (for application to the RAM 158) per unit of time and, in turn, the detail per frame, may be varied. Thus, assuming the RAM has 256 sample storage locations (addresses) and the user desires a one second acquisition time per data frame (i.e., per the 256 data points), a write clock rate of 256 Hz is necessitated; on the other hand, a user desiring to sacrifice detail for a data frame containing double the number of heart cycles would select a two second sweep (assuming a heart cycle duration of approximately one second) to obtain all 256 data points by adjusting the frequency of the clock 174 to 128 Hz.

Assuming that the user has made the selections indicated by the switch positions shown in FIG. 9, the discussion of the operation of the circuitry 19 in processing a frame of incoming heart data will now proceed. As will be seen, the completion of acquisition of a frame of data results in the resetting of the flip-flop 154. Thus, the $\bar{Q}$ output of the flip-flop 154 will be high upon the arrival of a mid-QRS pulse. The coincidence of the high $\bar{Q}$ of the flip-flop 154 and the mid-QRS pulse from the one-shot 148 will result in the passage of the mid-QRS pulse through the AND gate 152. The output of the AND gate 152 is applied, in one instance, to the FETs 86, 86$^1$ of the filter/amplifier 20 (and corresponding FETs of the filter/amplifier 26) to zero the filter/amplifiers as mentioned above. In addition to serving as the "zeroing" signal of the system, the pulse stream output of the AND gate 152 sets the frame clearing flip-flop 156 and resets (to a count of zero) both the read and write counters 170, 168 which, as just mentioned, were at maximum count (that is, 256 for purposes of the present example) as a result of the just-completed acquisition of an entire frame of data.

The frame clearing flip-flop 156 being set, its Q output applies a high signal to the gate of the FET 222 and to the OR gate 224. The FET 222 connects the input to the analog-to-digital converter 160 to ground. Thus, the signal from the flip-flop 156 ties the input to the analog-to-digital converter 160 to ground, isolating the analog ECG signal from the filter/amplifier 26 from the converter 160. At the same time, the OR gate 224 goes high. Its output, applied to the "read or write" terminal of the RAM 58, directs the RAM 158 to write new data into its addresses. In addition, the high Q output of the flip-flop 156 is applied to the OR gate 226, the output of which is applied to the "start conversion" terminal of the converter 160. Thus, the analog-to-digital converter 160 is directed to proceed to write the analog state existing at its input (ground or logic "zero") into a corresponding digital word. The output of the multiplexer 166 supplies addresses to the RAM 158, directing the data at its input to specific locations therein. The AND gate 228 is disabled by the low Q output of the reset flip-flop 154; thus, the multiplexer 166 is driven by the count of the read counter 170 insofar as the supply of addresses for entering the zero data input to the RAM 158. The read clock 172 runs at a much higher frequency than the variable write clock 174, driving the read counter 170 to a full count in about 30 milliseconds. Thus, after only 30 milliseconds, a zero has been written into every address of the RAM 158, clearing the formerly acquired frame of data from the RAM 158. The clear screen of the CRT 34 will reflect this "erasure" of data.

After the clearing of the RAM 158 as aforesaid, the read counter 170, having achieved maximum count (256), produces a "full" pulse signal which is applied to the reset port of the frame-clearing flip-flop 156. The flip-flop 156 having been reset, the now-high $\bar{Q}$ output thereof is simultaneously applied to the gate of the FET 220 and to the set terminal of the flip-flop 154. At the same time, the low Q output of the flip-flop 156, applied to the gate of the FET 222, disconnects the input of the analog-to-digital converter 160 from ground and, by means of the now-conducting FET 220, connects its input to the analog ECG signal from the filter/amplifier 26. The high Q output of the set flip-flop 154 enables the AND gate 228 so that write pulses (produced by the narrowing of the clock pulses from the variable write clock 174 by means of the one-shot 164) appear at the output of the AND gate 228. The output of the AND gate 228 is applied to the multiplexer 166, the write counter 168, and (via the OR gate 226) the "start conversion" port of the analog-to-digital converter 160. The coincidence of a pulse (i.e., logic "one" state) at the three aforesaid locations simultaneously commands (1) the start of the conversion of the ECG signal into a digital word, (2) the increase in the count of the write counter 168 by one and (3) the provision, by the multiplexer 166, of the new count of the write counter 168 to the RAM 158 as an address for the data point being converted from analog to digital. At the completion of the conversion of the amplitude of the ECG signal to a digital word, the analog-to-digital converter 160 applies a pulse to the OR gate 224. This pulse directs the RAM 158 to write the new data point into the address supplied by the multiplexer 166. As aforesaid, the address supplied will in such case be the just-incremented count of the write counter 168.

The above-described process will continue until the write counter 168 has counted a full frame of data into the RAM 158. At such time, the counter 168 will reset the flip-flop 154 so that the next arriving mid-QRS pulse from the one-shot 148. will set the frame clearing flip-flop 156, resulting in the writing of zeros into all addresses of the RAM, clearing the frame of data. The output of the RAM 158, representing, in digital words, the amplitude of the ECG (or EAHS in the event the front panel switch 36 is so set) is applied to a digital-to-analog converter 176 for subsequent application to the symmetrizing circuitry discussed above and, eventually, to the vertical deflection amplifier 144. (As the ECG position has been selected by the switch 36, no symmetrizing will be effected.) The count of the read counter 170, representing, in a digital word, the abscissa location of the associated ECG data point in the RAM 158, is applied to the digital-to-analog converter 178 to locate the ECG amplitude horizontally on the screen of the CRT 34. Over time, the words supplied by the counter 170 drive the horizontal deflection amplifier 180 to produce a sawtooth function indicating the steady horizontal progression of data points onto the screen of the CRT 34.

To obtain a "freeze-frame" of desired heart activity, the physician moves the switch 150 to the "Freeze" position which grounds, and, hence, inactivates the AND gate 152, blocking the mid-QRS pulses from passage through the gate. By so grounding the gate 152 it can be seen from the discussion, supra, that the data in the RAM 158 cannot be cleared as the flip-flop 156 will not reset. Repeated display of the most-recently acquired heart cycle data will occur by the continual application of the count of the read counter 170 to the RAM 158.

Although a specific implementation of a presently preferred embodiment of this invention is presented herein, it will be apparent to those skilled in the art that other specific implementations are available within the spririt and scope of these teachings. Also, while selective, full screen display of the respective electrical and audio characteristics of the heart affords effective use of small viewing screens providing easily viewed individual traces, in cases where the display screen is sufficiently large the traces may be displayed simultaneously.

The aforesaid advantages of the present system are seen to result, in large measure, from improvements in the methods and in the apparatus for generating displays and in the displays per se. The specific character of the display apparatus depends upon the type of display required or desired. In those instances where a permanent record may not be needed, a cathode ray tube display such as that disclosed will suffice. Where a permanent record is needed, a photographic record of the cathode ray tube display may be made, either in the freeze frame made of operation or other mode described herein, using old and well-established photographic techniques, such as exemplified in U.S. Pat. Nos. 2,457,774 and 2,294,015, for example. A separate cathode ray tube for photographic purposes as described in these patents is not a necessity. Similarly, a stylus graph recorder or other printout device using state of the art techniques, can be coupled to the output circuits of this heart activity analyzer to provide a tracing of the selected heart activity.

Further reductions in the size and weight of the present system are achievable by replacing the cathode ray tube and heart rate meter with a liquid crystal display such as a pictorial liquid crystal matrix display. Typical displays are described in "Liquid Crystal Pictorial Displays" by Michael N. Ernstoff, A1AA Digital Avionics System Conference Record, Paper 75-602, April 1975; U.S. Pat. No. 3,862,360; "Liquid Crystal Matrix Displays", Bernard J. Lechner, Frank J. Marlowe, Edward O. Nester and Juri Tults, IEEE, Vol. 59, Number 11, November 1971, Pages 1566–1579, and "LSI-LCD 10k Element Matrix Unit Displays TV Images", Electronic Engineering Times, Monday May 5, 1975, Page 21. This reduction in size is obtainable due to the smaller volume of the flat panel liquid display and its lower power requirement which permits the use of smaller batteries. This size reduction increases the portability and convenience of using the instrument.

Thus, it is seen that there has been brought to the medical instrumentation art a new and improved system for measuring and analyzing the activity of the heart. By means of a system incorporating the present invention, the practicing physician can perform indepth analyses of a patient's heart in his office without encountering the substantial space and energy consumption requirements attendant the use of present day phonocardiographs and the like.

What is claimed is:

1. Apparatus for producing and displaying an electrical signal indicative of the electrical energy characteristics of the heart, comprising:
   (a) a pickup device having pickup electrodes adapted for contact with the skin of a patient and having an output circuit;
   (b) an active circuit element coupled between one of said pickup electrodes and said output circuit and being in one state of electrical conduction when said pickup is not in contract with the skin of a patient and being in a different state of electrical conduction when said pickup electrodes are in contact with the skin of a patient;

(c) amplification and display means electrically coupled ot said output circuit for displaying the electical output of said pickup device; and
(d) control means responsive to the state of electrical conduction of said active element when said electrodes are in contact with the skin of a patient for lowering the frequency response of said amplification and display means.

2. Apparatus as set forth in claim 1 in which:
(a) said control means maintains a predetermined low frequency boundary of bandwidth range of said amplification means when said output circuit is in said one state of electical conduction and a lower low frequency boundary of bandwidth range of said amplification means when said output circuit is in said different state of electrical conduction.

3. Apparatus for producing and displaying an electrical signal indicative of the electrical energy characteristics of the heart of a body, comprising:
(a) circuit means including pickup means for producing electrical signals indicative of electrical energy characteristics of the heart and for producing a control signal having a first value when said pickup means is not in contact with the body and a second value when said pickup means is in contact with the body;
(b) amplification means having a controllable bandwidth range and responsive to said electrical signals;
(c) display means responsive to said amplification means for displaying said electrical signals; and
(d) control means responsive to said control signal for controlling the bandwidth range of said amplification means from a first low frequency boundary when said pickup means is not in contact with the body to a lower low frequency boundary when said pickup means is in contact with the body.

4. Apparatus as set forth in claim 3, in which:
(a) the first low frequency boundary of bandwidth range is about 5 Hz/sec. when said pickup means is not in contact with the body and the lower low frequency boundary of bandwidth range is about 0.05 Hz/sec. when said pickup means is in contact with the body.

* * * * *